United States Patent [19]

Okumura

[11] Patent Number: 4,857,358
[45] Date of Patent: Aug. 15, 1989

[54] POWDERY COMPOUND EMULISIFIER AND ITS PRODUCTION

[75] Inventor: Minoru Okumura, Hyogo, Japan

[73] Assignee: Kabushiki Kaisha Hayashibara Seibutsu Kagaku Kenkyujo, Okayama, Japan

[21] Appl. No.: 70,139

[22] Filed: Jun. 29, 1987

[30] Foreign Application Priority Data

Dec. 29, 1986 [JP] Japan .................................. 61-313324

[51] Int. Cl.$^4$ ......................... A23L 1/035; B01F 17/00
[52] U.S. Cl. .................................... 426/654; 426/553; 426/602; 426/660
[58] Field of Search ............... 426/603, 613, 604, 549, 426/556, 654, 658, 602, 660, 554, 553, 552; 252/351

[56] References Cited

U.S. PATENT DOCUMENTS

4,725,387  2/1988  Hirao et al. ...................... 426/48 X

Primary Examiner—Donald E. Czaja
Assistant Examiner—Celine T. Callahan
Attorney, Agent, or Firm—Browdy and Neimark

[57] ABSTRACT

Disclosed is a novel powdery compound emulsifier, obtained by adding crystalline alpha-maltose to a liquid or paste compound emulsifier containing two or more members selected from the group consisting of sucrose fatty acid esters, glycerine fatty acid esters and sorbitan fatty acid esters; and converting the crystalline alpha-maltose into crystalline beta-maltose hydrate to effect pulverization, as well as its preparation.

10 Claims, No Drawings

POWDERY COMPOUND EMULSIFIER AND ITS PRODUCTION

BACKGROUND OF THE INVENTION

1. Field of the Invention

The present invention relates to a powdery compound emulsifier, and its preparation and use.

More particularly, the present invention relates to a powdery compound emulsifier, obtained by pulverizing a liquid or paste compound emulsifier containing a surfactant selected from the group consisting of sucrose fatty acid esters, glycerine fatty acid esters and sorbitan fatty acid esters by the addition of crystalline alpha-maltose, as well as to the preparation and use of such compound.

2. Description of the Prior Art

In many emulsifiers for food products, cosmetics and pharmaceuticals, two or more surfactants are used in combination.

For example, in confectioneries or bakery products, a compound emulsifier containing two or more surfactants is used to improve the emulsifying and foaming powers of oil and fat, the storage stability of the emulsifier per se, the mechanical processibility of other materials such as wheat flour and starch, and the quality and shelf life of the final products.

Since in this case homogenization of different surfactants is difficult, propylene glycol or sorbitol is used in combination and the use leads to a compound emulsifier in paste.

Compound emulsifier in paste, however, has the drawbacks that it is inconvenient to handle; that it is difficult to divide by weight; and that it requires a relatively high skill in mixing it together with powder materials such as starch and wheat flour.

In order to overcome these drawbacks of conventional compound emulsifiers, various compound emulsifiers in powder have been proposed.

Japanese patent publication No. 5,705/68 proposes that a mixture of two melted surfactants and anhydrous crystalline glucose is pulverized and mixed with wheat flour. Japanese patent publication No. 23,023/72 proposes that a syrup of food-grade surfactants, prepared in the presence of a saccharide, is mixed with egg and dehydrated at below 60° C. Japanese patent publication No. 19,873/74 proposes that a mixture solution prepared by dissolving surfactants and mannitol in warm water is spray-dried. Japanese patent laid-open No. 93,686/79 proposes that a mixture of beta-cyclodextrin, food-grade surfactants and either or both of melted saccharide and/or melted sugar alcohol is cooled and pulverized.

Conventional powdery compound emulsifier has drawbacks in that its preparation is relatively complicated; it exerts unsatisfactory emulsifying and foaming powers; and it is unsatisfactory in storage ability. These render the use of compound emulsifier paste unavoidable.

SUMMARY OF THE INVENTION

In view of the foregoing, I investigated the possibility of using saccharides in a compound emulsifier containing surfactants, in particular, those selected from the group consisting of sucrose fatty acid esters, glycerine fatty acid esters and sorbitan fatty acid esters, in order to develop a novel powdery compound emulsifier that is satisfactory in emulsifying and foaming powers and superior in storage stability.

Our investigation revealed that crystalline alpha-maltose is superior to the other saccharides tested.

I found that a superior powdery compound emulsifier is successfully obtained by adding crystalline alpha-maltose to a liquid or paste compound emulsifier containing two or more members selected from the group consisting of sucrose fatty acid esters, glycerine fatty acid esters and sorbitan fatty acid esters; and converting the crysrtalline alpha-maltose into crystalline beta-maltose hydrate to effect pulverization.

Also, it was found that an edible premix powder of high commercial value is conveniently prepared by the addition of the powdery compound emulsifier.

DETAILED DESCRIPTION OF THE INVENTION

The working "liquid or paste compound emulsifier" as referred to in the invention designates a substantially homogeneous liquid or paste containing two or more members selected from the group consisting of sucrose fatty acid esters, glycerine fatty acid esters and sorbitan fatty acid esters.

One or more of other surfactants, for example, propylene glycol fatty acid ester, calcium lactate fatty acid ester and lecithin, can be advantageously used in combination with any of the above described surfactants. If the surfactant to be used is solid or semisolid and this hinders homogenization with other surfactant, the surfactant should be prepared as a liquid or paste by adding it to an appropriate amount of water, and dissolving the resultant mixture by heating.

In this case, either of ethyl alcohol, maltose, oil and fat may be added together with water in an amount, desirably, less than that of water, in order to accelerate the homogenization or to stabilize the dissolved surfactants.

Since this addition of ethyl alcohol, maltose, oil, and fat renders the use of propylene glycol and sorbitol optional, the conversion of crystalline alpha-maltose into crystalline beta-maltose hydrate form is not affected by the presence of any of these substances. Thus, a stable compound emulsifier powder is easily obtainable.

Furthermore, the present invention is characterized in that crystalline alpha-maltose is an edible nutriment.

A liquid or paste compound emulsifier is pulverized by adding thereto crystalline alpha-maltose thereof, and allowing the crystalline alpha-maltose to convert to crystalline beta-maltose hydrate while accelerating the conversion by ageing at a temperature of about 20°–70° C. for about 0.1–5 days.

The amount of crystalline alpha-maltose is from about 0.5- to 15-times, desirably, from 0.8- to 10-time of that of the liquid or paste compound emulsifier.

Crystalline alpha-maltose may be a crystalline alpha-maltose powder as disclosed in Japanese patent laid-open No. 35,800/86, or that commercialized by Hayashibara Co., Ltd., Okayama, Japan, under the trade name of "FINETOSE ®".

The wording "converting crystalline alpha-maltose into crystalline beta-maltose hydrate to effect pulverization" as referred to in the invention includes the following two cases: In one of the cases, a paste compound emulsifier wherein crystalline alpha-maltose has been converted in part into crystalline beta-maltose hydrate is pulverized, for example, by spray-drying, and the resultant emulsifier is solidified and tempered. In the other case, a solid compound emulsifier wherein crystalline alpha-maltose has been simultaneously converted into crystalline beta-maltose hydrate is pulverized, for example, by means of cutting or scraping the solid emulsifier. Either case leads to a stable emulsifier powder.

The obtained powder may be subjected to dehydrating, screening and granulating steps in order to augment its quality.

The compound emulsifier of the invention is in the stable nonhygroscopic powder, and is easily mixable with other powder materials.

The present emulsifier exerts sufficient emulsifying and foaming powers, and is excellent in storage stability. Thus, it is advantageously usable in food products, cosmetics and pharmaceuticals.

In food products, the present emulsifier improves the emulsifying and foaming powers of oil and fat, the mechanical processibility of food materials such as starch and wheat flour, and the quality and shelf life of the final products. For example, premix powders for use in confectionaries, bakery products, noodles and vermicelli can be prepared by adding the present emulsifier to one or more powder materials such as starch, wheat flour, rye flour, barley flour, corn flour or soybean flour, if necessary, together with one or more of dried yeast, baking powder, defatted milk, seasoning, fortifier, quality-improving agent, coloring agent and flavoring agent.

In cosmetics, the present emulsifier improves the emulsifying and cleansing powers, the dispersibility of oil-soluble substances in water, and the affinity of the cosmetic ingredients to the skin, as well as imparting appropriate gloss and texture.

In pharmaceuticals, the present emulsifier improves the affinity and absorption of the effective ingredients to or by the cells and tissues, as well as improving the mechanical processibility.

The following Experiments will explain the present invention.

fatty acid ester commercialized by Dai-ichi Kogyo Seiyaku Co., Ltd., was added with 30 parts of either saccharide as listed in Table I, along with 35 parts of water, and the resultant was mixed by heating to 90°–95° C. to obtain a homogeneous compound emulsifier in paste.

In the specification, "part(s)" is expressed by weight, unless specified otherwise.

Experiment 2

Preparation of powdery compound emulsifier

One part of a paste compound emulsifier, obtained by the method in Experiment 1, was kneaded with 3 parts of a fresh saccharide of the same type as used to prepare the compound emulsifier, and the mixture was allowed to stand at 35° C. for one day. The resultant was fed to a pulverizer to obtain a powdery compound emulsifier. The obtained powdery compound emulsifiers were rated "impossible", "possible" and "easy" with respect to pulverizability that varied with the type of the saccharide used. The results were as shown in Table I.

Experiment 3

Comparison of emulsifying and foaming powers

Powdery compound emulsifier, obtained by the method in Experiment 2, were tested for emulsifying and foaming powers.

Three-hundred and sixty parts of whole egg, 280 parts of sucrose, 33 parts of either powdery compound emulsifier, 240 parts of wheat flour and 72 parts of water were placed in a mixer, and whipped for six minutes. The resultant barrier was tested for specific volume as a criterion of emulsifying and foaming powers.

After straining with a 20-mesh screen, the batter was tested again for specific volume as a criterion of foam stability.

As control, a paste compound emulsifier using crystalline alpha-maltose as described in Experiment 2 was used after equalizing the amounts of surfactants. The results were as shown in Table I.

TABLE I

| Saccharide | Pulverizability | Specific volume of batter (cc/g) | | Remarks |
| --- | --- | --- | --- | --- |
| | | On whipping | On straining | |
| Xylose | Impossible | — | — | Control |
| Anhydrous crystalline glucose | Easy | 1.64 | 1.60 | Control |
| Crystalline glucose hydrate | Possible | 1.56 | 1.49 | Control |
| Fructose | Impossible | — | — | Control |
| Sorbitol | Impossible | — | — | Control |
| Mannitol | Impossible | — | — | Control |
| Crystalline alpha-maltose | Easy | 2.33 | 2.31 | Present invention |
| Crystalline beta-maltose hydrate | Possible | 1.85 | 1.82 | Control |
| Sucrose | Impossible | — | — | Control |
| Lactose | Possible | 1.82 | 1.77 | Control |
| Palatinose | Impossible | — | — | Control |
| Maltitol | Impossible | — | — | Control |
| beta-Cyclodextrin | Easy | 1.35 | 1.33 | Control |
| Without saccharide | — | 2.33 | 2.30 | — |

Experiment 1

Preparation of paste emulsifier

A mixture of 20 parts of "DK ESTER F110", a sucrose fatty acid ester commercialized by Dai-ichi Kogyo Seiyaku Co., Ltd., Kyoto, Japan, 5 parts of "SUNSOFT No. 8,000", a glycerine mono fatty acid ester commercialized by Taiyo Kagaku Co., Ltd., Mie, Japan, and 10 parts of "SORGEN 90", a sorbitan mono These data show that the use of either anhydrous crystalline glucose, crystalline alpha-maltose or beta-cyclodextrin facilitated pulverization of paste compound emulsifier.

Comparison of the obtained emulsifiers on their emulsifying and foaming powders in terms of specific volume of batter provided that only crystalline alpha-maltose was superior and the other saccharides were extremely inferior.

It was found that a powdery compound emulsifier using crystalline alpha-maltose was superior in foam stability, as well as exerting a relatively high specific volume of batter.

The above confirmed that crystalline alpha-maltose was a superior pulverizing material for liquid or paste compound emulsifier.

Standing tests at ambient temperature revealed that the present emulsifier retained its high foaming power and foam stability as found instantly on preparation over a period of six months.

Several embodiments according to the invention will hereinafter be described.

EXAMPLE 1

Powdery compound emulsifier

Thirty parts of sucrose fatty acid ester, 10 parts of glycerine mono fatty acid ester, 10 parts of sorbitan mono fatty acid ester, 30 parts of crystalline alpha-maltose and 40 parts of water were mixed to homogeneity by heating to 90°-95° C. similarly as in Experiment 1, and the resultant paste was kneaded with 180 parts of crystalline alpha-maltose powder. The resultant was solidified by two-day standing at 30° C.

The resultant solid contained crystalline beta-maltose hydrate converted from the crystalline alpha-maltose. The solid was fed to a pulverizer to obtain a powdery compound emulsifier.

The product was sufficient in emulsifying and foaming powers, and excellent in storage stability.

The product is advantageously usable in food products in general such as confectioneries and bakery products, as well as in detergents, cosmetics and pharmaceuticals.

EXAMPLE 2

Powdery compound emulsifier

Twenty parts of sucrose fatty acid ester, 10 parts of glycerine mono hardened beef tallow fatty acid ester, 8 parts of sorbitan monostearate, 30 parts of crystalline beta-maltose hydrate, 5 parts of lard and 70 parts of water were mixed by heating similarly as in Example 1, and the resultant liquid compound emulsifier was mixed with 420 parts of crystalline alpha-maltose powder. The resultant was solidified by one-day standing at 35° C., and fed to a pulverizer to obtain a powdery compound emulsifier.

The product was sufficient in emulsifying and foaming powers, and excellent in storage stability.

Similarly as the product in Example 1, the product is advantageously usable in food products, cosmetics and pharmaceuticals.

EXAMPLE 3

Powdery compound emulsifier

Twenty parts of glycerine monopalmitate, 25 parts of calcium stearyl lactate, 3 parts of sorbitan mono beef tallow fatty acid ester, 30 parts of crystalline alpha-maltose, 5 parts of shortening, 5 parts of alcohol and 40 parts of water were mixed by heating similarly as in Example 1, and the resultant paste compound emulsifier was mixed with 200 parts of crystalline alpha-maltose. The resultant was solidified and pulverized similarly as in Example 1 to obtain a powdery compound emulsifier.

The product was sufficient in emulsifying power, and excellent in foam stability.

The product is advantageously usable to improve the quality of bakery products and the mechanical processibility of the dough therefor.

EXAMPLE 4

Premix powder

One hundred parts of wheat flour, 70 parts of sucrose, 40 parts of maltose, 6 parts of a powdery compound emulsifier obtained by the method in Example 1, 2 parts of powdered defatted milk and 0.15 parts of powdered vanilla flavor were mixed to homogeneity, and aliquots of the resultant mixture were packed.

A mixture of 100 parts of the product, 70 parts of whole egg and 14 parts of water was whipped in usual manner, and the resultant dough was baked to obtain a sponge cake.

The sponge cake had a smooth texture, and excellent taste and flavor.

EXAMPLE 5

Premix powder

One hundred parts of wheat flour, 8 parts of sucrose, 8 parts of powdered shortening, 4 parts of powdered defatted milk, 2 parts of kitchen salt and one part of a powdery compound emulsifier obtained by the method in Example 3 were mixed to substaantial homogeneity, and aliquots of the resultant mixture were packed to obtain a premix powder for use in bakery products.

A dough, obtained by adding 100 parts of the premix powder to 6 parts of raw yeast and 44 parts of water in usual manner, was mixed with 40 parts of margarine, and the resultant was shaped and baked to obtain a croissant.

The croissant was soft and full, and excellent in taste and flavor.

Effects of the Invention

As described above, in the pulverization of a liquid or paste compound emulsifier containing two or more members selected from the group consisting of sucrose fatty acid esters, glycerine fatty esters and sorbitan fatty esters, by adding crystalline alpha-maltose thereto, and converting it into crystalline beta-maltose hydrate, a powdery compound emulsifier having sufficient emulsifying and foaming powers and an excellent storage stability can be easily obtained.

The present compound emulsifier is in stable and nonhygroscopic powder form, and it is advantageously usable in food products, cosmetics and pharmaceuticals.

Since the present compound emulsifier is easily mixable with other powder materials, it can be advantageously mixed with starch and/or wheat flour in the preparation of premix powders, for example, those for confectioneries and bakery.

While preferred embodiments have been described, variations thereto will occur to those skilled in the art within the scope of the present inventive concepts which are delineated by the following claims.

I claim:

1. A powdery compound emulsifier, obtained by adding crystalline alpha-maltose to a liquid or paste compound emulsifier containing at least two members selected from the group consisting of sucrose fatty acid ester, glycerine fatty acid ester and sorbitan fatty acid ester; and pulverizing the resultant mixture by allowing the crystalline alpha-maltose to convert into crystalline beta-maltose hydrate.

2. The powdery compound emulsifier of claim 1, wherein said liquid or paste compound emulsifier is prepared by adding water to a compound emulsifier containing at least two surfactants to form an aqueous mixture; and dissolving said mixture by heating.

3. The powdery compound emulsifier of claim 1, wherein said liquid or paste compound emulsifier contains water together with a member selected from the group consisting of ethyl alcohol, maltose, oil and fat.

4. A process for preparing a powdery compound emulsifier, comprising:
adding 0.5 to 15 parts by weight of crystalline alpha-maltose to one part by weight of a liquid or paste compound emulsifier containing at least two members selected from the group consisting of sucrose fatty acid ester, glycerine fatty acid ester and sorbitan fatty acid ester; and
ageing the resultant mixture at a temperature of 20°–70° C. from 1 to 5 days to allow the crystalline alpha-maltose to convert to crystalline beta-maltose hydrate to effect pulverization of the mixture.

5. The process of claim 4, wherein said liquid or paste compound emulsifier is prepared by adding water to a compound emulsifier containing at least two surfactants to form a mixture; and dissolving the mixture by heating.

6. The process of claim 4, wherein said liquid or paste compound emulsifier contains water and a member of the group consisting of ethyl alcohol, maltose, oil and fat.

7. The process of claim 4, wherein the amount of crystalline alpha-maltose is from 0.5- to 15-fold by weight of that of the liquid or paste compound emulsifier.

8. A process for preparing a premix powder for use in food products, comprising:
adding to at least one powder material a powdery compound emulsifier obtained by adding 0.5 to 15 parts by weight of crystalline alpha-maltose to a liquid or paste compound emulsifier containing at least two members selected from the group consisting of sucrose fatty acid ester, glycerine fatty acid ester and sorbitan fatty acid ester; and ageing the resultant mixture at a temperature of 20°–70° C. from 0.1 to 5 days to allow the crystalline alpha-maltose to convert to crystalline beta-maltose hydrate to effect pulverization of the mixture.

9. The process of claim 8, wherein said liquid or paste compound emulsifier is prepared by adding water to a compound emulsifier containing at least two surfactants to form a mixture; and dissolving the mixture by heating.

10. The process of claim 8, wherein said liquid or paste compound emulsifier contains water and a solvent selected from the group consisting of ethyl alcohol, maltose, oil and fat.

* * * * *